US012765774B2

(12) United States Patent
Koide

(10) Patent No.: US 12,765,774 B2
(45) Date of Patent: Oct. 20, 2026

(54) WEARABLE RING FOR VEIN DETECTION WITH REFLECTIVE MEMBER ADJACENT TO OPTICAL SENSOR

(71) Applicant: Japan Display Inc., Tokyo (JP)

(72) Inventor: Gen Koide, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 18/946,377

(22) Filed: Nov. 13, 2024

(65) Prior Publication Data

US 2025/0064319 A1 Feb. 27, 2025

Related U.S. Application Data

(63) Continuation of application No. PCT/JP2023/017851, filed on May 12, 2023.

(30) Foreign Application Priority Data

May 17, 2022 (JP) ................................ 2022-080974

(51) Int. Cl.
*A61B 5/00* (2006.01)

(52) U.S. Cl.
CPC .......... *A61B 5/0059* (2013.01); *A61B 5/6826* (2013.01); *A61B 2562/164* (2013.01); *A61B 2562/166* (2013.01)

(58) Field of Classification Search
None
See application file for complete search history.

(56) References Cited

U.S. PATENT DOCUMENTS 10,966,643 B1 * 4/2021 Vavadi ................. A61B 5/4845
2003/0118219 A1 6/2003 Higuchi et al.
2009/0027358 A1 1/2009 Hosono
2016/0309068 A1 * 10/2016 Nadeau .................. A61B 1/043
2018/0211020 A1 7/2018 Fukuda et al.
2020/0000345 A1 * 1/2020 Connor .............. A61B 5/14532
(Continued)

FOREIGN PATENT DOCUMENTS

JP 2003-141514 A 5/2003
JP 2005242907 A * 9/2005
(Continued)

OTHER PUBLICATIONS

Search Report issued in related International Application No. PCT/JP2023/017851, mailed on Jun. 13, 2023 and English translation of same. 5 pages.

(Continued)

*Primary Examiner* — Keith M Raymond
*Assistant Examiner* — Ashish S. Jasani
(74) *Attorney, Agent, or Firm* — K&L Gates LLP

(57) ABSTRACT

According to an aspect, a detection device includes: a housing; a light source that is provided in the housing so as to be capable of irradiating an irradiation side outside the housing; an optical sensor that is provided so as to be arranged alongside the light source in a first direction of the housing and is capable of detecting light incident from the irradiation side of the light source; and a reflective member that is provided in the housing so as to be located between the light source and the optical sensor and is capable of reflecting the incident light toward the irradiation side of the light source.

7 Claims, 9 Drawing Sheets

(56) References Cited

U.S. PATENT DOCUMENTS

| | | | | |
|---|---|---|---|---|
| 2021/0305320 | A1* | 9/2021 | Lim | H10K 85/40 |
| 2021/0379388 | A1* | 12/2021 | Connor | A61M 60/531 |

FOREIGN PATENT DOCUMENTS

| | | | |
|---|---|---|---|
| JP | 2009-032005 | A | 2/2009 |
| WO | WO2008/044697 | A1 | 4/2008 |
| WO | WO2017/010305 | A1 | 1/2017 |

OTHER PUBLICATIONS

Office Action issued in related Japanese Patent Application No. 2024-521718 issued on Nov. 18, 2025 and English translation of same. 6 pages.

* cited by examiner

WEARABLE RING FOR VEIN DETECTION WITH REFLECTIVE MEMBER ADJACENT TO OPTICAL SENSOR

CROSS-REFERENCE TO RELATED APPLICATION

This application claims the benefit of priority from Japanese Patent Application No. 2022-080974 filed on May 17, 2022 and International Patent Application No. PCT/JP2023/017851 filed on May 12, 2023, the entire contents of which are incorporated herein by reference.

BACKGROUND

1. Technical Field

What is disclosed herein relates to a detection device.

2. Description of the Related Art

Optical sensors capable of detecting fingerprint patterns and vein patterns are known (refer to, for example, Japanese Patent Application Laid-open Publication No. 2009-032005). Among such optical sensors, sensors are known each including a plurality of photodiodes in which an organic semiconductor material is used as an active layer. The organic semiconductor material is disposed between lower and upper electrodes, and signal lines are electrically coupled to the lower electrodes of the photodiodes to output detection signals to a detection circuit.

In conventional technologies, as the distance between a light source and an optical sensor increases, the amount of light reaching the optical sensor exponentially decreases. For this reason, conventional detection devices are required to arrange the light source and the optical sensor in a housing so as to improve accuracy of detection.

For the foregoing reasons, there is a need for a detection device that can improve accuracy of detection using a light source and an optical sensor accommodated in a housing.

SUMMARY

According to an aspect, a detection device includes: a housing; a light source that is provided in the housing so as to be capable of irradiating an irradiation side outside the housing; an optical sensor that is provided so as to be arranged alongside the light source in a first direction of the housing and is capable of detecting light incident from the irradiation side of the light source; and a reflective member that is provided in the housing so as to be located between the light source and the optical sensor and is capable of reflecting the incident light toward the irradiation side of the light source.

According to an aspect, a detection device includes: a housing; a light source that is provided in the housing so as to be capable of irradiating an irradiation side outside the housing; an optical sensor that is provided so as to be arranged alongside the light source in a first direction of the housing and is capable of detecting light incident from the irradiation side of the light source; and a cover provided in the housing so as to protrude from the housing while covering the light source. The cover includes: a cover body that protrudes from the housing and is capable of making contact with an object to be measured; an opening that is formed at a portion of the cover body configured to make contact with the object to be measured and is configured to allow the light emitted by the light source to exit therefrom toward the outside of the cover body; and a reflective layer that is provided on an inner surface of the cover body and is capable of reflecting the light emitted by the light source to focus the light on the opening.

DETAILED DESCRIPTION

Figure 1:
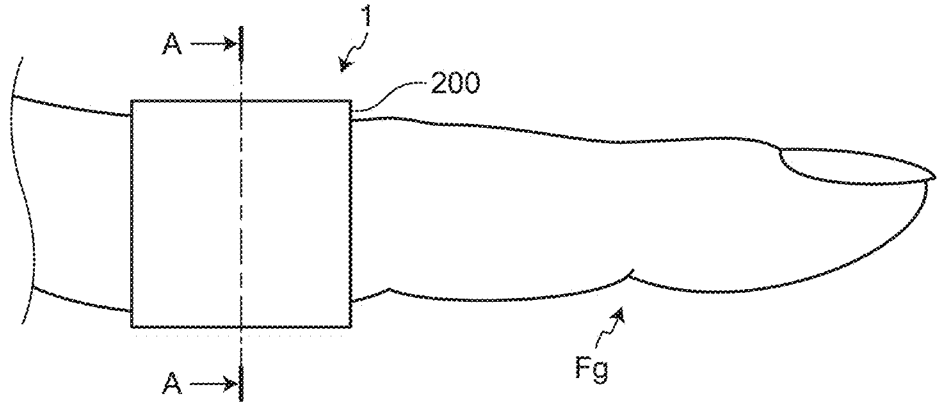
FIG. 1 is a schematic view illustrating an exemplary external appearance when a state of a finger accommodated inside a detection device according to a first embodiment is viewed from a lateral side of a housing.

The following describes modes (embodiments) for carrying out the disclosure in detail with reference to the drawings. The present disclosure is not limited to the description of the embodiments given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the present specification and the drawings, and detailed description thereof may not be repeated where appropriate.

In the present specification and claims, in expressing an aspect of disposing another structure on or above a certain structure, a case of simply expressing "on" includes both a case of disposing the other structure immediately on the certain structure so as to contact the certain structure and a case of disposing the other structure above the certain structure with still another structure interposed therebetween, unless otherwise specified.

First Embodiment

Detection Device

Figure 2:
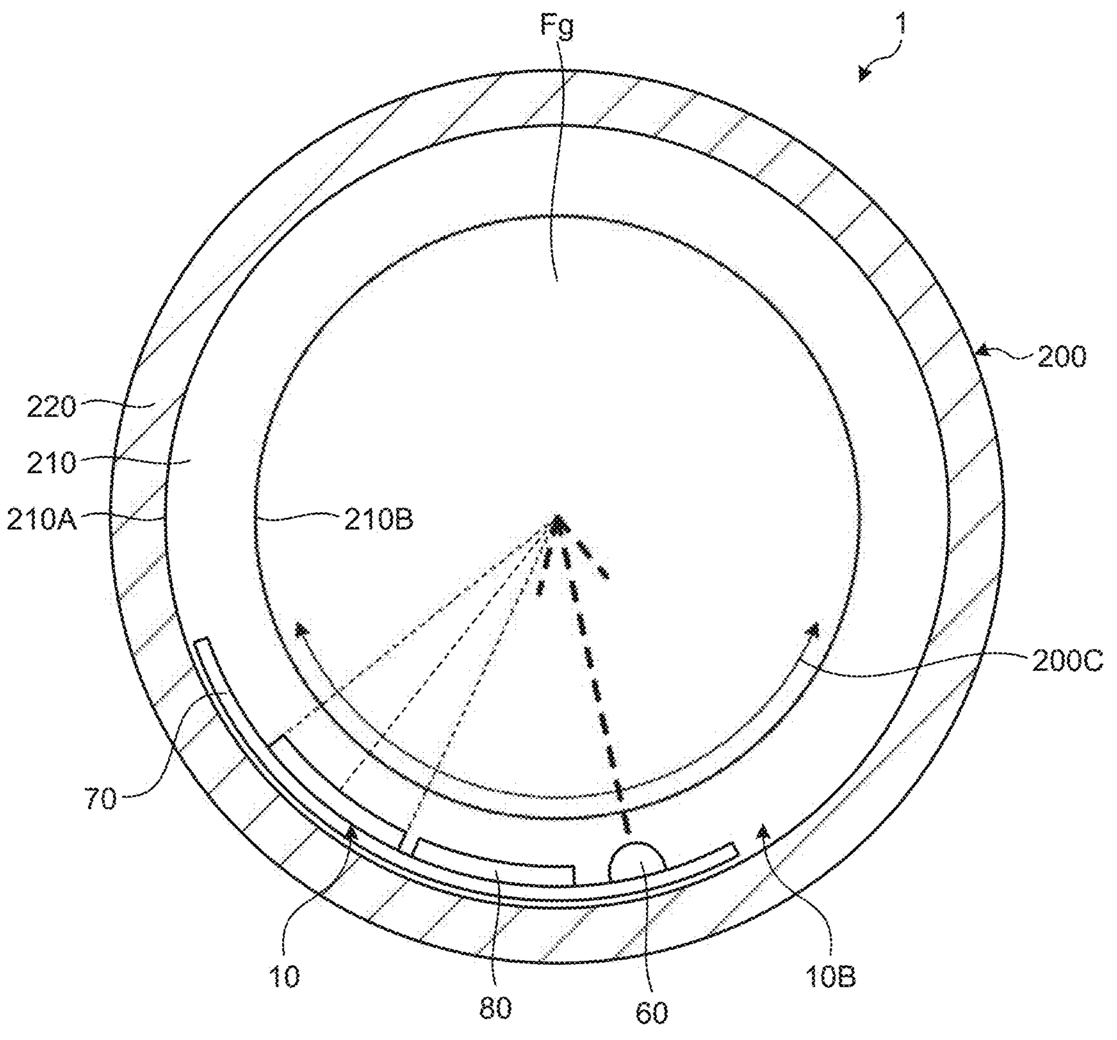
FIG. 2 is a schematic sectional view taken along section A-A illustrated in FIG. 1.
Figure 3:
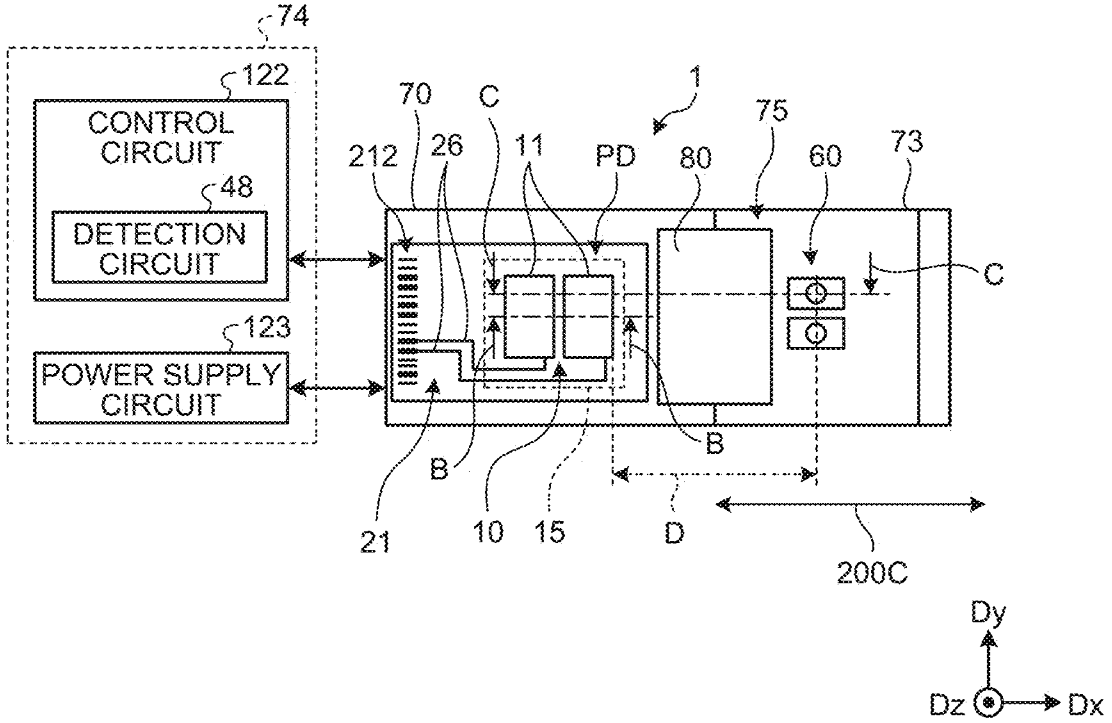
FIG. 3 is a schematic diagram illustrating an exemplary configuration of an optical sensor and a light source of the detection device illustrated in FIG. 1.
Figure 4:
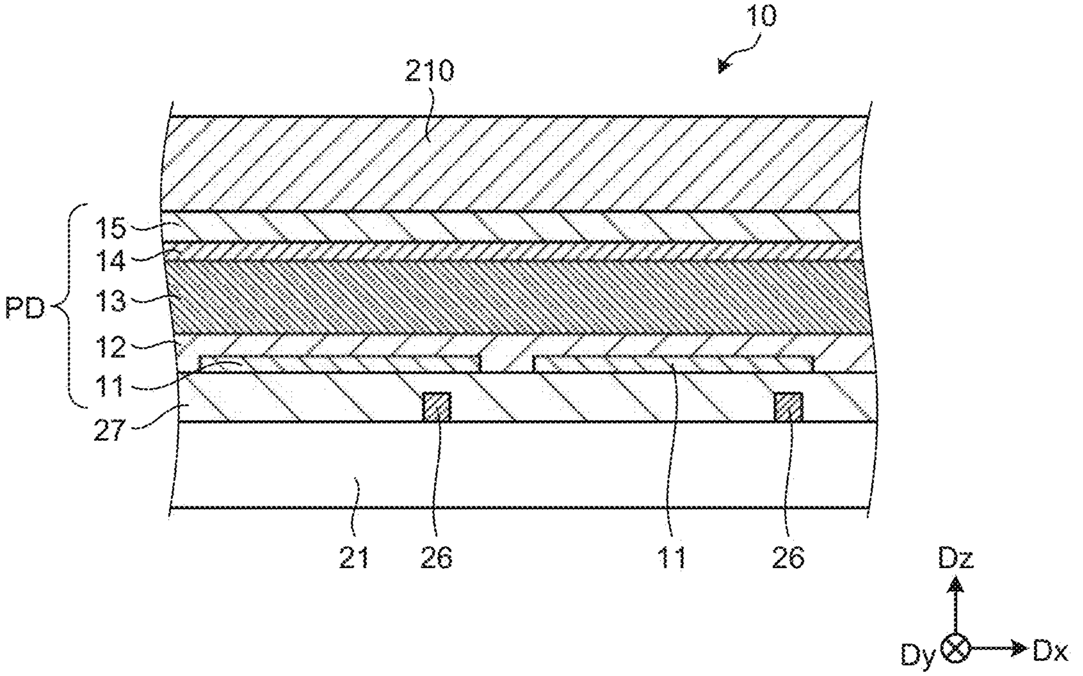
FIG. 4 is a schematic sectional view illustrating an exemplary multilayer configuration of the optical sensor taken along section B-B illustrated in FIG. 3.

FIG. 1 is a schematic view illustrating an exemplary external appearance when a state of a finger accommodated inside a detection device according to a first embodiment is viewed from a lateral side of a housing. FIG. 2 is a schematic sectional view taken along section A-A illustrated in FIG. 1. FIG. 3 is a schematic diagram illustrating an exemplary configuration of an optical sensor and a light source of the detection device illustrated in FIG. 1. FIG. 4 is a schematic sectional view illustrating an exemplary multilayer configuration of the optical sensor taken along section B-B illustrated in FIG. 3. FIG. 2 illustrates only the basic configuration of the detection device according to the first embodiment and does not illustrate the other configurations.

A detection device 1 illustrated in FIG. 1 is a finger ring-shaped device that can be worn on and removed from a human body and is worn on a finger Fg of the human body. Examples of the finger Fg include a thumb, an index finger, a middle finger, a ring finger, and a little finger. The human body is a person to be authenticated whose identity is verified by the detection device 1. The detection device 1 can detect biometric information on a living body from the finger Fg wearing the detection device. The finger Fg is an example of a measurement target. The measurement target is the living body or a part of the living body, and is an object to be measured. The detection device 1 is made into a finger ring or a wristband so as to be easily carried by a user. In the following description, the detection device 1 is assumed to be used as the finger ring. The detection device 1 can use the detected biometric information for authentication of the person to be authenticated.

As illustrated in FIG. 2, the detection device 1 includes a housing 200, a light source 60, an optical sensor 10, and a reflective member 80. The detection device 1 is a device that includes a battery (not illustrated) in the housing 200 and is operated by power from the battery.

The housing 200 is formed in a ring shape (annular shape) that can be worn on the finger Fg, and is a wearable member to be worn on the living body. In the example illustrated in FIG. 2, the housing 200 includes a first housing 210 and a second housing 220. The first housing 210 is integrated with the second housing 220 to form the housing 200 into the ring shape. The first housing 210 is a member that makes contact with the human body wearing the housing 200. The first housing 210 accommodates therein the light source 60, the optical sensor 10, the reflective member 80, and so forth. The first housing 210 is formed into a ring shape using a housing material such as a light-transmitting synthetic resin or silicon. The second housing 220 has a surface of the housing 200 that covers an outer peripheral surface 210A of the first housing 210. The second housing 220 is formed into a ring shape using a member of, for example, a metal or a non-light-transmitting synthetic resin. The first housing 210 of the housing 200 accommodates therein a flexible printed circuit board 70 on which the light source 60, the optical sensor 10, and so forth are mounted. The flexible printed circuit board 70 is accommodated in the housing 200, for example, by forming the housing 200 by filling the periphery of the flexible printed circuit board 70 formed into a ring shape with a filling member in a mold.

As illustrated in FIG. 3, the flexible printed circuit board 70 is formed into a deformable band shape. The flexible printed circuit board 70 has a first mounting area 73 and a second mounting area 74. The first mounting area 73 is provided on a front surface side of the flexible printed circuit board 70 and is an area where the light source 60 and so forth are mounted. The second mounting area 74 is provided on a back surface side of the flexible printed circuit board 70 and is an area where a control circuit 122, a power supply circuit 123, and so forth are mounted. The flexible printed circuit board 70 electrically couples the light source 60, the optical sensor 10, and so forth to the control circuit 122 and the power supply circuit 123.

In the following description, a first direction Dx is one direction in a plane parallel to the flexible printed circuit board 70 and is the same direction as a circumferential direction 200C. A second direction Dy is one direction in the plane parallel to the flexible printed circuit board 70 and is a direction orthogonal to the first direction Dx. The second direction Dy may non-orthogonally intersect the first direction Dx. A third direction Dz is a direction orthogonal to the first direction Dx and the second direction Dy. The third direction Dz is a direction normal to the flexible printed circuit board 70. The term "plan view" refers to a positional relation when viewed in a direction orthogonal to the flexible printed circuit board 70 and a sensor substrate 21.

In the present embodiment, the optical sensor 10 is provided on the flexible printed circuit board 70 alongside the light source 60 in the circumferential direction 200C along the first direction Dx. By being disposed close to the light source 60 in the circumferential direction 200C, the optical sensor 10 can detect light that has been emitted by the light source 60 and reflected by the finger Fg (human body).

The sensor substrate 21 is an insulating substrate and is formed, for example, of a film-like resin into a band shape. The sensor substrate 21 is a deformable substrate on which the optical sensor 10 is mounted. The sensor substrate 21 is mounted on the flexible printed circuit board 70, whereby the optical sensor 10 is disposed close to the light source 60 in the circumferential direction 200C of the housing 200. The sensor substrate 21 has an area in which the optical sensor 10 is mounted.

In the present embodiment, as illustrated in FIG. 2, the flexible printed circuit board 70 is accommodated in the housing 200 such that the front surface provided with the optical sensor 10, the reflective member 80, and the light source 60 faces an inner peripheral surface 210B of the housing 200. When the flexible printed circuit board 70 has a light-transmitting property, the optical sensor 10, the reflective member 80, and the light source 60 may be mounted on the back surface opposite the front surface. In that case, the light source 60 only needs to be disposed such that light is emitted toward the flexible printed circuit board 70 and light transmitted through the flexible printed circuit board 70 is emitted toward outside the housing 200.

As illustrated in FIG. 2, the light source 60 is provided in the first housing 210 of the housing 200, and is configured to be capable of emitting light toward the center of the housing 200. For example, inorganic light-emitting diodes (LEDs) or organic electroluminescent (EL) diodes (organic light-emitting diodes (OLEDs)) are used as the light source 60. The light source 60 emits light having predetermined wavelengths. In the present embodiment, the light source 60 includes a plurality of light sources so as to be capable of emitting near-infrared light, red light, and green light.

The light emitted from the light source 60 is reflected by a surface of an object to be detected, such as the finger Fg, and enters the optical sensor 10. Alternatively, the light emitted from the light source 60 may be reflected in the finger Fg or the like, or transmitted through the finger Fg or the like and enter a plurality of photodiodes PD of the optical sensor 10. Thereby, the detection device 1 can detect the information on the living body in the finger Fg or the like. Examples of the information on the living body include, but are not limited to, pulse waves, pulsation, and a vascular image of the finger or a palm. That is, the detection device 1 may be configured as a vein detection device that detects biometric information on veins or the like. When detecting a fingerprint or a vascular pattern of the object to be detected, the photodiodes PD of the optical sensor 10 of the detection device 1 are arranged in a matrix having a row-column configuration.

The optical sensor 10 is a sensor that is provided in the first housing 210 of the housing 200 and is capable of detecting light incident from an irradiation side of the light source 60. The irradiation side of the light source 60 is the inside of the ring-shaped housing 200 and is a side that irradiates the finger Fg serving as the measurement target wearing the housing 200. The optical sensor 10 detects the light emitted by light source 60 and reflected by the finger Fg or the like, light directly incident on the optical sensor, and other light. The optical sensor 10 is organic photodiodes (OPDs). Since the sensor substrate 21 is attached to the flexible printed circuit board 70, the optical sensor 10 is provided in the housing 200 so as to be arranged alongside the light source 60 in the circumferential direction 200C (first direction Dx) of the housing 200.

As illustrated in FIG. 3, the optical sensor 10 includes the photodiodes PD that are the organic photodiodes. The optical sensor 10 has a configuration including two lower electrodes 11 arranged along the circumferential direction 200C. The optical sensor 10 is mounted on one sensor substrate 21 and is electrically coupled to the flexible printed circuit board 70 via the sensor substrate 21. The optical sensor 10 has a configuration in which the two lower electrodes 11 arranged in the first direction Dx and one upper electrode 15 are stacked together. The upper electrode 15 covers the two lower electrodes 11 in plan view.

The sensor substrate 21 includes a coupling portion 212 The coupling portion 212 is electrically coupled to the control circuit 122, the power supply circuit 123, and so forth. The coupling portion 212 is electrically coupled to wiring lines 26 provided on the sensor substrate 21. The wiring lines 26 are each a shield layer formed of, for example, metal wiring, and are formed of a material having better conductivity than each of the lower electrodes 11 of the photodiodes PD. The wiring lines 26 are provided in a layer between the sensor substrate 21 and the photodiodes PD in the third direction Dz. The sensor substrate 21 electrically couples the coupling portion 212 to the upper electrode 15 via a power line (not illustrated) and supplies a sensor power supply signal (sensor power supply voltage) from the power supply circuit 123 to the upper electrode 15 via the coupling portion 212. With this configuration, the upper electrode 15 of the optical sensor 10 is supplied with the sensor power supply signal from the power supply circuit 123 via a power supply electrode 211.

As illustrated in FIG. 4, the optical sensor 10 includes the photodiodes PD. In the present embodiment, the optical sensor 10 further includes the wiring lines 26 and an insulating layer 27. The insulating layer 27 is provided on the sensor substrate 21 so as to cover the wiring lines 26. The insulating layer 27 may be an inorganic insulating film or an organic insulating film. The wiring lines 26 may be formed in the same layer as the lower electrode 11.

The photodiode PD is provided on the insulating layer 27. The photodiode PD includes the lower electrode 11, a lower buffer layer 12, an active layer 13, an upper buffer layer 14, and the upper electrode 15. As the photodiode PD, the lower electrode 11, the lower buffer layer 12 (hole transport layer), the active layer 13, the upper buffer layer 14 (electron transport layer), and the upper electrode 15 are stacked in this order in the third direction Dz orthogonal to the sensor substrate 21.

The lower electrode 11 is an anode electrode of the photodiode PD, and is formed of, for example, a light-transmitting conductive material such as indium tin oxide (ITO). The active layer 13 changes in characteristics (for example, voltage-current characteristics and resistance value) according to light emitted thereto. An organic material is used as a material of the active layer 13. Specifically, the active layer 13 has a bulk heterostructure containing a mixture of a p-type organic semiconductor and an n-type fullerene derivative ((6,6)-phenyl-$C_{61}$-butyric acid methyl ester (PCBM)) that is an n-type organic semiconductor. As the active layer 13, low-molecular-weight organic materials can be used including, for example, fullerene ($C_{60}$), phenyl-$C_{61}$-butyric acid methyl ester (PCBM), copper phthalocyanine (CuPc), fluorinated copper phthalocyanine ($F_{16}CuPc$), 5,6,11,12-tetraphenyltetracene (rubrene), and perylene diimide (PDI) (derivative of perylene).

The active layer 13 can be formed by a vapor deposition process (dry process) using any of the low-molecular-weight organic materials listed above. In this case, the active layer 13 may be, for example, a multilayered film of CuPc and $F_{16}CuPc$, or a multilayered film of rubrene and $C_{60}$. The active layer 13 can also be formed by a coating process (wet process). In this case, the active layer 13 is made using a material obtained by combining any of the above-listed low-molecular-weight organic materials with a high-molecular-weight organic material. As the high-molecular-weight organic material, for example, poly(3-hexylthiophene) (P3HT) and F8-alt-benzothiadiazole (F8BT) can be used. The active layer 13 can be a film made of a mixture of P3HT and PCBM, or a film made of a mixture of F8BT and PDI.

The lower buffer layer 12 is a hole transport layer. The upper buffer layer 14 is an electron transport layer. The lower buffer layer 12 and the upper buffer layer 14 are provided to facilitate holes and electrons generated in the active layer 13 to reach the lower electrode 11 or the upper electrode 15. The lower buffer layer 12 (hole transport layer) is in direct contact with the top of the lower electrode 11, and is also provided in an area between the adjacent lower electrodes 11. The active layer 13 is in direct contact with the top of the lower buffer layer 12. The material of the hole transport layer is a metal oxide layer. For example, tungsten oxide ($WO_3$) or molybdenum oxide is used as the metal oxide layer.

The upper buffer layer 14 (electron transport layer) is in direct contact with the top of the active layer 13, and the upper electrode 15 is in direct contact with the top of the upper buffer layer 14. Polyethylenimine ethoxylated (PEIE) is used as a material of the electron transport layer.

The materials and the manufacturing methods of the lower buffer layer 12, the active layer 13, and the upper buffer layer 14 are merely exemplary, and other materials and manufacturing methods may be used. For example, each of the lower buffer layer 12 and the upper buffer layer 14 is not limited to a single-layer film, but may be formed as a multilayered film that includes an electron block layer and a hole block layer.

The upper electrode 15 is provided on the upper buffer layer 14. The upper electrode 15 is a cathode electrode of the photodiode PD, and is continuously formed over the entire first and second optical sensors 10A and 10B. In other words, the upper electrode 15 is continuously provided on the photodiodes PD. The upper electrode 15 faces the lower electrodes 11 with the lower buffer layer 12, the active layer 13, and the upper buffer layer 14 interposed therebetween. The upper electrode 15 is formed, for example, of a light-transmitting conductive material such as ITO or indium zinc oxide (IZO). The upper electrode 15 is electrically coupled to the power supply circuit 123 via the coupling portion 212. In the first optical sensor 10A, the photodiode PD is well sealed by providing the first housing 210 on the upper electrode 15 and so forth.

As illustrated in FIG. 3, the reflective member 80 is disposed between the light source 60 and the optical sensor 10 in the circumferential direction 200C (first direction Dx) of the housing 200, and can reflect incident light toward the irradiation side of the light source 60. The incident light includes, for example, light (reflected light) incident from the finger Fg and light directly incident from the light source 60. In the example illustrated in FIG. 3, the reflective member 80 reflects the incident light toward the inner peripheral surface 210B (inside) of the housing 200. In the present embodiment, the reflective member 80 is formed as a reflective layer having reflectance of 50% or more between the light source 60 and the optical sensor 10 on the flexible printed circuit board 70. The reflective member 80 can be formed as the reflective layer using, for example, a highly reflective metal material such as Al or Ag, or a dielectric multilayer film that reflects light in the wavelength range of the light source. For example, a reflective plate formed of a metal such as Al or an Al alloy having metallic luster, paint, a mirror, or the like may be provided as the reflective member 80 on the flexible printed circuit board 70. The reflective member 80 is provided so as to cover an area 75 between the light source 60 and the photodiode PD on the flexible printed circuit board 70. The area 75 is a rectangular area of the flexible printed circuit board 70 defined by a distance D in the first direction Dx and the length of the width in the second direction Dy of the flexible printed circuit board 70.

In the present embodiment, the distance D is the distance from the center of the light source 60 to one end of the lower electrode 11 of the nearest photodiode PD, but is not limited thereto. For example, the distance D may be the distance from an end of the light source 60 to an end of the optical sensor 10 opposed thereto, the distance from the center or an end of the light source 60 to an end of the sensor substrate 21 opposed thereto, or the like.

The reflective member 80 may be provided so as to cover the entire area 75 or may be provided so as to cover a part of the area 75. In the present embodiment, the length in the first direction Dx of the reflective member 80 is nearly equal to the distance D. The length in the second direction Dy of the reflective member 80 is smaller than the length (width) of the flexible printed circuit board 70 and larger than the length of the sensor substrate 21. The length in the second direction Dy of the reflective member 80 may be smaller than the length (width) of the flexible printed circuit board 70 and larger than or equal to the length of the photodiode PD.

The wiring lines 26 of the sensor substrate 21 are coupled to a detection circuit 48 included in the control circuit 122 via a plurality of signal lines of the flexible printed circuit board 70. In other words, the detection circuit 48 is electrically coupled to the lower electrodes 11 of the optical sensor 10 via the signal lines. The detection circuit 48 may be formed as a separate circuit from the control circuit 122.

The control circuit 122 is a circuit that controls detection operations by supplying control signals to the photodiodes PD. Each of the photodiodes PD outputs an electrical signal corresponding to the light emitted thereto as a detection signal Vdet to the detection circuit 48. In the present embodiment, the detection signals Vdet of the photodiodes PD are sequentially output to the detection circuit 48 in a time-divisional manner. In other words, the signal lines are sequentially electrically coupled to the detection circuit 48 in a time-divisional manner. The detection device 1 thereby detects information on the object to be detected based on the detection signals Vdet from the photodiodes PD. The control circuit 122 is operated by power supplied from the power supply circuit 123.

The detection circuit 48 is an analog front-end (AFE) circuit, for example. The detection circuit 48 is a signal processing circuit having functions of at least a detection signal amplifier and an analog-to-digital (A/D) converter. The detection signal amplifier amplifies the detection signals Vdet. The A/D converter converts analog signals output from the detection signal amplifier into digital signals.

The exemplary configuration of the detection device 1 according to the present embodiment has been described above. The configuration described above using FIGS. 1 to 4 is merely an example, and the configuration of the detection device 1 according to the present embodiment is not limited to the example. The configuration of the detection device 1 according to the present embodiment can be flexibly modified according to specifications and/or operations.

Distance Between Light Source and Optical Sensor of Detection Device

The following describes the distance D between the light source 60 and the optical sensor 10 of the detection device 1. For example, in the detection device 1, when the light source 60 is too close to the optical sensor 10, a larger proportion of light reaching the optical sensor 10 passes near a surface of the finger Fg with fewer blood vessels, whereby the signal level of the biometric information decreases, thus disabling normal sensing. For this reason, the distance between the light source 60 and the optical sensor 10 usually needs to be approximately 5 mm or more. In the detection device 1, as the light source 60 becomes farther from the optical sensor 10, the amount of light absorbed by the human body increases, and the amount of light reaching the optical sensor 10 exponentially decreases, so that a larger amount of light of the light source is required.

Figure 5:
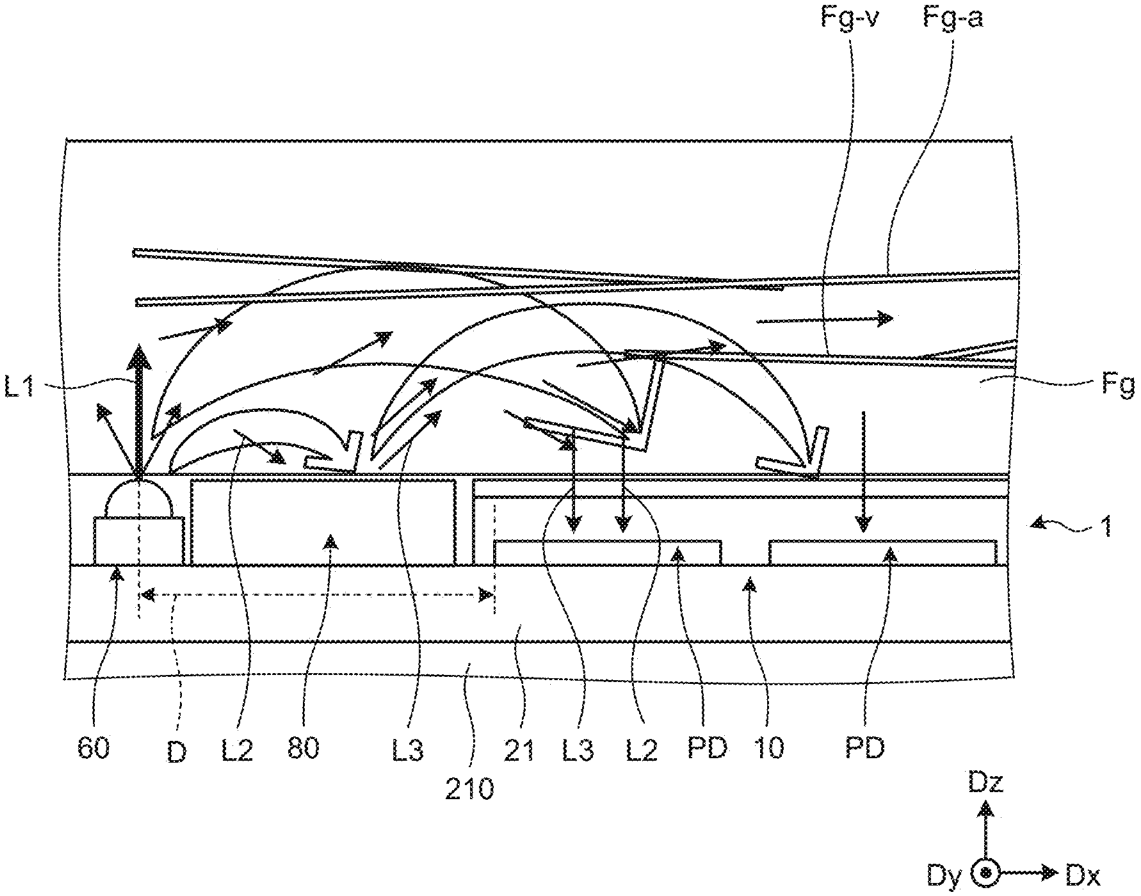
FIG. 5 is a schematic sectional view illustrating an exemplary configuration of the detection device taken along section C-C illustrated in FIG. 3.

FIG. 5 is a schematic sectional view illustrating an exemplary configuration of the detection device 1 taken along section C-C illustrated in FIG. 3. In the detection device 1 illustrated in FIG. 5, the distance D between the light source 60 and the optical sensor 10 is 5 mm. In the detection device 1, the reflective member 80 is located so as to cover a surface of the sensor substrate 21 between the light source 60 and the optical sensor 10. In the detection device 1, when the light source 60 emits light L1 while the detection device 1 is worn on the finger Fg, the light L1 passes through the housing 200 and is applied to the finger Fg. The light L1 enters the inside of the finger Fg through the skin and is transmitted through or reflected by muscle tissues, arteries Fg-a, veins Fg-v, and the like. Reflected light L2 obtained by reflecting the light L1 in the finger Fg travels toward the inner side of the finger Fg or toward the detection device 1. If the optical sensor 10 of the detection device 1 is placed at a destination of the light L2 emitted outward from the finger Fg, the photodiodes PD of the detection device 1 receive the reflected light L2. If the reflective member 80 of the detection device 1 is placed at a destination of the reflected light L2 emitted outward from the finger Fg, the reflected light L2 is incident on the reflective member 80 and reflected by the reflective member 80, and enters the inside of the finger Fg again. Reflected light L3 obtained by reflecting the reflected light L2 in the finger Fg travels toward inside the finger Fg or toward the detection device 1. If the optical sensor 10 of the detection device 1 is placed at a destination of the reflected light L3 emitted outward from the finger Fg, the photodiodes PD of the detection device 1 receive the reflected light L3. The photodiodes PD of the optical sensor 10 of the detection device 1 can thus receive the reflected light L2 and the reflected light L3 reflected by the reflective member 80.

Figure 6:
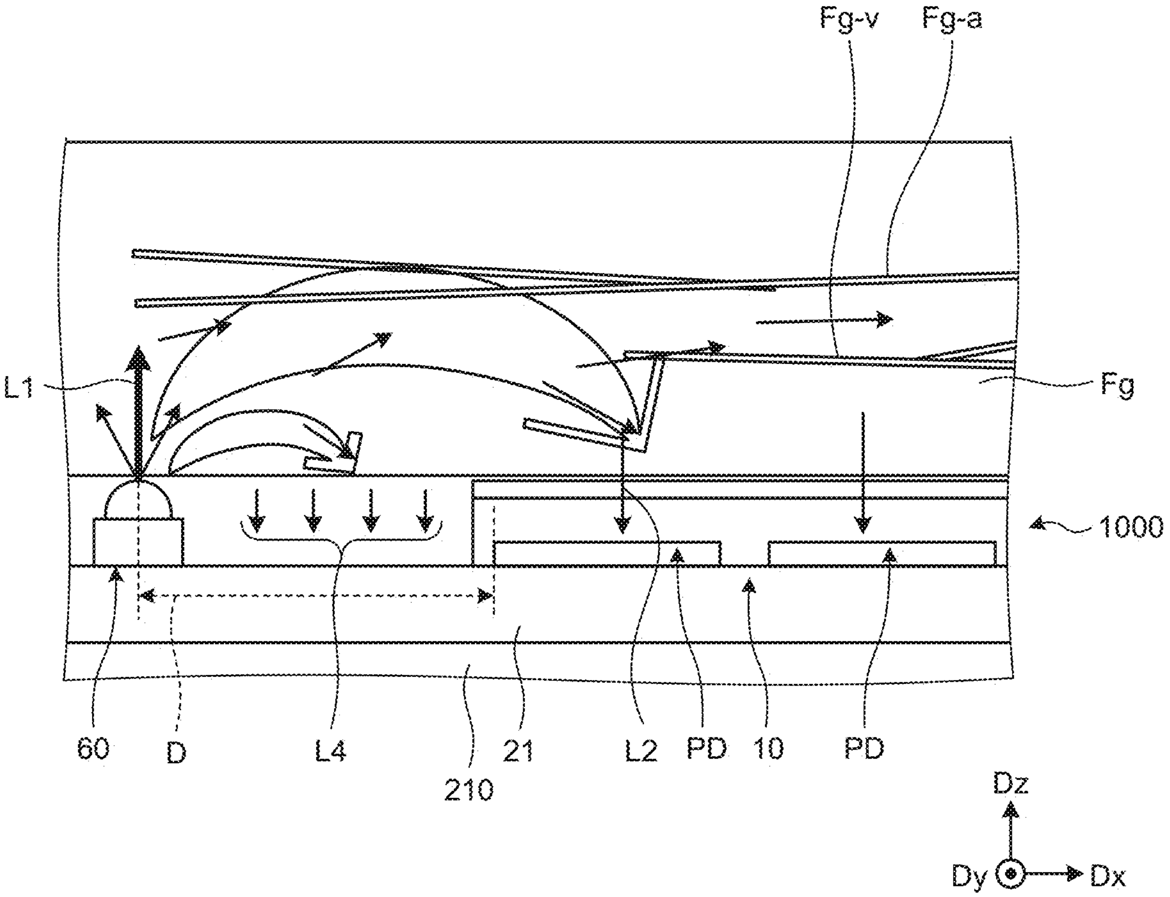
FIG. 6 is a schematic sectional view for explaining an exemplary effect of light of a comparative detection device according to the first embodiment.

In contrast, a case where the detection device 1 does not include the reflective member 80 will be described. FIG. 6 is a schematic sectional view for explaining an exemplary effect of light of a comparative detection device 1000 according to the first embodiment. The comparative detection device 1000 illustrated in FIG. 6 has the same basic configuration as the detection device 1 of the first embodiment, and differs in configuration from the detection device 1 in not including the reflective member 80.

In the comparative detection device 1000 illustrated in FIG. 6, the distance D between the light source 60 and the optical sensor 10 is 5 mm. In the comparative detection device 1000, the surface of the sensor substrate 21 between the light source 60 and the optical sensor 10 is exposed. In the comparative detection device 1000, when the light source 60 emits the light L1 while the detection device 1 is worn on the finger Fg, the light L1 passes through the housing 200 and is applied to the finger Fg. The light L1 enters the inside of the finger Fg through the skin and is transmitted through and reflected by the muscle tissues, the arteries Fg-a, and the veins Fg-v. The reflected light L2 obtained by reflecting the light L1 in the finger Fg travels toward the inner side of the finger Fg or toward the comparative detection device 1000. If the optical sensor 10 of the comparative detection device 1000 is placed at a destination of the light L2 emitted outward from the finger Fg, the photodiodes PD of the comparative detection device 1000 receive the reflected light L2. However, the optical sensor 10 does not receive reflected light L4 that travels from the finger Fg toward the sensor substrate 21 between the light source 60 and the optical sensor 10. Therefore, in the comparative detection device 1000, the optical sensor 10 cannot receive the reflected light L4 reflected in the finger Fg and loses the reflected light L4.

The detection device 1 according to the first embodiment will be compared with the comparative detection device 1000. In the detection device 1, the optical sensor 10 can receive the reflected light L2 and the reflected light L3 reflected by the reflective member 80 of the light L1 emitted from the light source 60 into the finger Fg. However, since the comparative detection device 1000 does not include the reflective member 80, the comparative detection device 1000 receives only the reflected light L2 and cannot receive the reflected light L4 of the light L1 emitted from the light source 60 into the finger Fg. For this reason, the detection device 1 can receive an amount of light larger than that of the comparative detection device 1000 by the amount of light of the reflected light L3 reflected by the reflective member 80. Thus, the detection device 1 can reduce the loss of light between the light source 60 and the optical sensor 10 by providing the reflective member 80 between the light source 60 and the optical sensor 10. As a result, the detection device 1 can improve the accuracy of the detection using the light source 60 and the optical sensor 10 accommodated in the housing 200.

The detection device 1 can reduce the loss of light reaching the optical sensor 10 even when the distance D between the light source 60 and the optical sensor 10 is separated by 5 mm or more, thus improving the accuracy of detecting light from the light source 60 with the ring-shaped housing 200. The detection device 1 can thereby detect the peak of the perfusion index (PI) value when the distance D between the light source 60 and the optical sensor 10 is from 5 mm to 15 mm, so that the accuracy of detection can be further improved.

In the detection device 1, the reflective member 80 has reflectance of 50% or more. For example, since the veins Fg-v and the like are present in the finger Fg, the light L1 that has entered the interior of the finger Fg is reflected in various directions. The detection device 1 can reflect the reflected light L2 toward the finger Fg even if the reflected light L2 enters the reflective member 80 at various angles of incidence from the finger Fg. The detection device 1 can thereby improve the accuracy of detection of the light from the light source 60 even when the housing 200 is worn on the measurement target such as the finger Fg.

In the detection device 1, the optical sensor 10 is organic photodiodes. This configuration allows the detection device 1 to accurately detect the light reflected by the finger Fg, using the optical sensor 10.

In the detection device 1, the optical sensor 10 and the light source 60 are provided on the flexible printed circuit board 70, the lower electrodes 11 of the optical sensor 10 are electrically coupled to the wiring lines 26, and the wiring lines 26 are electrically coupled to the flexible printed circuit board 70. This configuration allows the detection device 1 to be manufactured by accommodating the flexible printed circuit board 70 in the housing 200, so that the productivity can be improved.

In the detection device 1, the housing 200 is formed in a ring shape. With this configuration, even when a space is provided between the light source 60 and the optical sensor 10 in the ring-shaped housing 200 of the detection device 1, the reflective member 80 is provided between the light source 60 and the optical sensor 10. Therefore, the accuracy of detection of the light emitted toward the finger Fg by the light source 60 can be improved.

Second Embodiment

If the distance D between the light source 60 and the optical sensor 10 is too small, the photodiode PD of the optical sensor 10 closest to the light source detects less blood vessel information than the photodiode PD at the other location, thus making the pulse waves difficult to be measured. The optical absorbance of human tissue is high, and the amount of light passing therethrough exponentially decreases with the distance D between the light source 60 and the optical sensor 10. Therefore, the following describes a configuration of a detection device according to a second embodiment in which the light source 60 is closer to the optical sensor 10 than in the first embodiment.

Detection Device According to Second Embodiment

Figure 7:
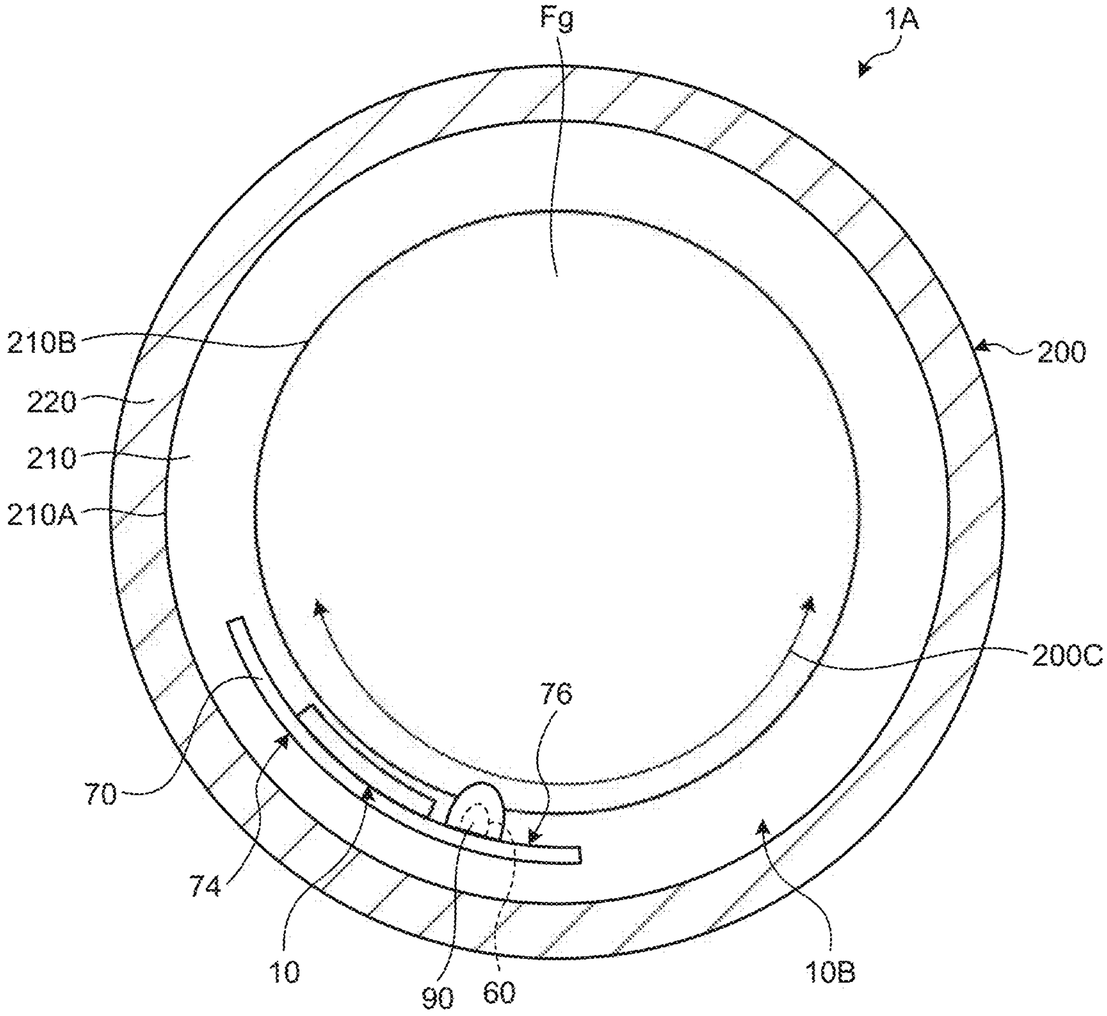
FIG. 7 is a schematic sectional view of a detection device according to a second embodiment taken along section A-A illustrated in FIG. 1.
Figure 8:
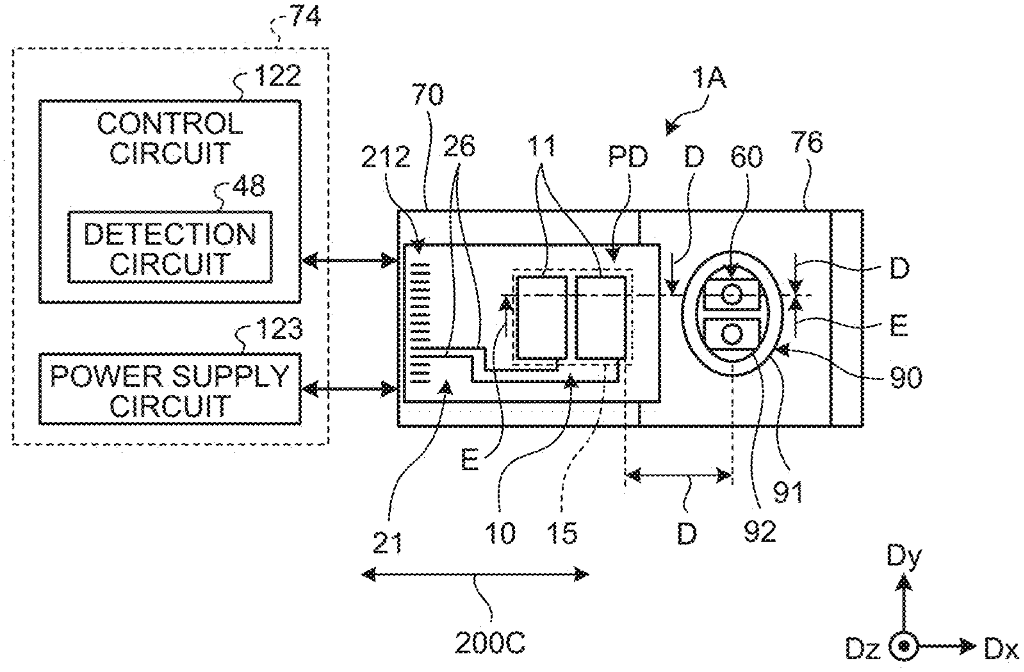
FIG. 8 is a schematic diagram illustrating an exemplary configuration of the optical sensor and the light source of the detection device illustrated in FIG. 7.
Figure 9:
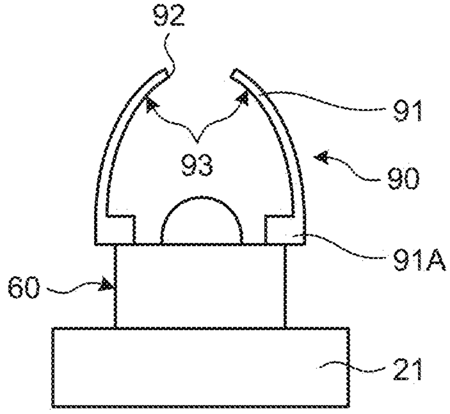
FIG. 9 is a schematic sectional view of the light source and a cover taken along section D-D illustrated in FIG. 8.

FIG. 7 is a schematic sectional view of the detection device according to the second embodiment taken along section A-A illustrated in FIG. 1. FIG. 7 illustrates only the basic configuration of the detection device according to the second embodiment and does not illustrate the other configurations. FIG. 8 is a schematic diagram illustrating an exemplary configuration of the optical sensor and the light source of a detection device 1A illustrated in FIG. 7. FIG. 9 is a schematic sectional view of the light source and a cover taken along section D-D illustrated in FIG. 8.

As with the detection device 1 of the first embodiment, the detection device 1A illustrated in FIG. 7 is a finger ring-shaped device that can be worn on and removed from the human body and is worn on the finger Fg of the human body. The detection device 1A can detect the biometric information on the living body from the finger Fg wearing the detection device 1A. The detection device 1A includes the housing 200, the light source 60, the optical sensor 10, and a cover 90.

The housing 200 includes the first housing 210 and the second housing 220 in the same way as the housing 200 according to the first embodiment. The first housing 210 is integrated with the second housing 220 to form the housing 200 into the ring shape. The first housing 210 is a member that makes contact with the human body wearing the housing 200. The first housing 210 accommodates therein the light source 60, the optical sensor 10, and so forth. The first housing 210 leaves one portion of the cover 90 to protrude outward from the inner peripheral surface 210B and accommodates therein the other portion of the cover 90. That is, the first housing 210 has a configuration in which the one portion of the cover 90 protrudes from the inner peripheral surface 210B, and the cover 90 can be pressed against the finger Fg when the housing 200 is worn on the finger Fg.

As illustrated in FIG. 8, the flexible printed circuit board 70 is formed into a deformable band shape. The flexible printed circuit board 70 has the second mounting area 74 and a third mounting area 76. The second mounting area 74 is provided on the back surface side of the flexible printed circuit board 70 and is the area where the control circuit 122, the power supply circuit 123, and so forth are mounted. The third mounting area 76 is an area that is provided on the front surface side of the flexible printed circuit board 70 and in which the light source 60 and so forth are mounted and the cover 90 is provided. The flexible printed circuit board 70 electrically couples the light source 60, the optical sensor 10, and so forth to the control circuit 122 and the power supply circuit 123. The flexible printed circuit board 70 is accommodated in the housing 200 such that the back surface faces the inner peripheral surface 210B of the housing 200. That is, the housing 200 accommodates therein the flexible printed circuit board 70 so that the one portion of the cover 90 protrudes from the inner peripheral surface 210B.

The optical sensor 10 is a sensor that is provided in the housing 200 so as to be arranged alongside the light source 60 in the circumferential direction 200C (first direction Dx) of the housing 200 and is capable of detecting the light incident from the irradiation side of the light source 60. The optical sensor 10 is provided on the flexible printed circuit board 70 so as to be arranged alongside the light source 60 in the circumferential direction 200C along the first direction Dx. By being disposed close to the light source 60 in the circumferential direction 200C, the optical sensor 10 can detect the light that has been emitted by the light source 60 and reflected by the finger Fg (human body). In the detection device 1A, the amount of light reaching the optical sensor 10 from the light source 60 is restrained from decreasing by setting the distance D between the light source 60 and the optical sensor 10 to 5 mm or less, The optical sensor 10 detects the light emitted by the light source 60 and reflected by the finger Fg or the like, light directly incident on the optical sensor, and other light. The optical sensor 10 is organic photodiodes. Since the sensor substrate 21 is attached to the flexible printed circuit board 70, the optical sensor 10 is provided in the housing 200 so as to be arranged alongside the light source 60 in the circumferential direction 200C (first direction Dx) of the housing 200. The optical sensor 10 includes the photodiodes PD that are the organic photodiodes (refer to FIG. 3) as is the case with the first embodiment.

As illustrated in FIG. 4, the optical sensor 10 includes the sensor substrate 21 and the photodiode PD. The photodiode PD has a configuration in which the lower electrode 11, the lower buffer layer 12 (hole transport layer), the active layer 13, the upper buffer layer 14 (electron transport layer), and the upper electrode 15 are stacked in this order in the third direction Dz orthogonal to the sensor substrate 21. In the present embodiment, the optical sensor 10 further includes the wiring lines 26 and the insulating layer 27.

The sensor substrate 21 is a deformable substrate on which the optical sensor 10 is mounted. The sensor substrate 21 is mounted on the flexible printed circuit board 70, whereby the optical sensor 10 is disposed close to the cover 90 in the circumferential direction 200C of the housing 200. The sensor substrate 21 locates the optical sensor 10 on the flexible printed circuit board 70 such that the distance D between the optical sensor 10 and the light source 60 covered by the cover 90 is 5 mm or less.

The light source 60 is covered by the cover 90 on the sensor substrate 21 so as to prevent the emitted light from directly reaching the optical sensor 10. The light source 60 includes a plurality of light sources so as to be capable of emitting near-infrared light, red light, and green light. The light emitted from the light source 60 exits from an opening 92 of a cover body 91 of the cover 90 toward the outside of the housing 200, is reflected by the surface of the object to be detected, such as the finger Fg, and enters the optical sensor 10. Of the light emitted from the light source 60, light that travels toward the optical sensor 10 is blocked by the cover 90.

The sensor substrate 21 has the same configuration as in the first embodiment. In the second embodiment, the sensor substrate 21 is disposed so as to be partially stacked on the third mounting area 76 of the flexible printed circuit board 70 so that the optical sensor 10 is located closer to the cover 90. This configuration makes the distance D between the light source 60 and the optical sensor 10 to be equal to or smaller than 5 mm in the detection device 1A.

As illustrated in FIG. 9, the cover 90 is provided so as to protrude from a housing 200 while covering the light source 60. The cover 90 includes the cover body 91, the opening 92, and a reflective layer 93. The cover body 91 is formed into a hollow hemispherical shape using a light-blocking member of a synthetic resin or a metal, for example. In the present embodiment, a case will be described where the cover body 91 is formed into a circular shape in plan view, but may be formed, for example, into a quadrilateral shape, a triangular shape, or a polygonal shape. That is, the cover body 91 may be formed into a shape of, for example, a circular cylinder, a triangular prism, a polygonal prism. The cover body 91 is formed to have strength that does not allow the cover body 91 to be crushed even when touched by the finger Fg or the like, for example. In the present embodiment, a fixing portion 91A formed at an end of the cover body 91 is fixed to the light source 60, but the fixing position is not limited thereto. The fixing portion 91A of the cover body 91 may be fixed to the sensor substrate 21 or may be provided to be fixed to the housing 200.

The opening 92 is formed at a portion of the cover body 91 that makes contact with the finger Fg as the measurement target, and allows the light emitted by the light source 60 to exit therefrom toward the outside of the cover body 91. The opening 92 is a through-hole in the cover body 91 through which the light emitted by the optical sensor 10 exits toward the outside of the housing 200. The opening 92 is formed at a top portion of the cover body 91 that faces the light source 60. The top portion of the cover body 91 is a portion that makes contact with the finger Fg as the measurement target. In the present embodiment, the opening 92 is formed into a circular shape, but may be formed, for example, into a quadrilateral shape, a triangular shape, or a polygonal shape. The opening 92 of the cover 90 may be covered with a light-transmitting member.

The reflective layer 93 is a reflective member that is provided on an inner surface of the cover body 91 and can reflect the light emitted by the light source 60 and focus it on the opening 92. The reflective layer 93 is provided on the inner surface so as to reflect the light emitted from the light source 60. The reflective layer 93 is formed on the inner surface of the cover body 91 using a highly reflective metal material such as Al or Ag, a dielectric multilayer film that reflects light in the wavelength range of the light source, or the like. The reflective layer 93 has reflectance of 50% or more. When the reflective layer 93 is totally reflective, the cover body 91 may be formed of a light-transmitting member. The reflective layer 93 can increase the amount of outgoing light from the opening 92 by reflecting the light emitted by the light source 60. When the cover body 91 is formed of a reflective metal, the reflective layer 93 may be the inner surface of the cover body 91.

In the example illustrated in FIG. 8, the distance D is the distance from the center of the light source 60 to one end of the lower electrode 11 of the nearest photodiode PD. The distance D between the light source 60 and the optical sensor 10 is 5 mm or less. Although the light source 60 is away from the optical sensor 10, the distance D can be reduced in the circumferential direction 200C by bringing the optical sensor 10 into contact with the cover 90.

The wiring lines 26 of the sensor substrate 21 are coupled to the detection circuit 48 included in the control circuit 122 via the signal lines of the flexible printed circuit board 70. In other words, the detection circuit 48 is electrically coupled to the lower electrodes 11 of the optical sensor 10 via the signal lines. The detection circuit 48 may be formed as a separate circuit from the control circuit 122.

The detection device 1A includes the control circuit 122 and the power supply circuit 123 described in the first embodiment. The control circuit 122 includes the detection circuit 48. The detection device 1A detects the information on the object to be detected based on the detection signals Vdet from the photodiodes PD. The control circuit 122 is operated by the power supplied from the power supply circuit 123.

The exemplary configuration of the detection device 1A according to the second embodiment has been described above. The configuration described above using FIGS. 7 to 9 is merely an example, and the configuration of the detection device 1A according to the present embodiment is not limited to the example. The configuration of the detection device 1A according to the present embodiment can be flexibly modified according to specifications and/or operations.

Distance Between Light Source and Optical Sensor of Detection Device

Figure 10:
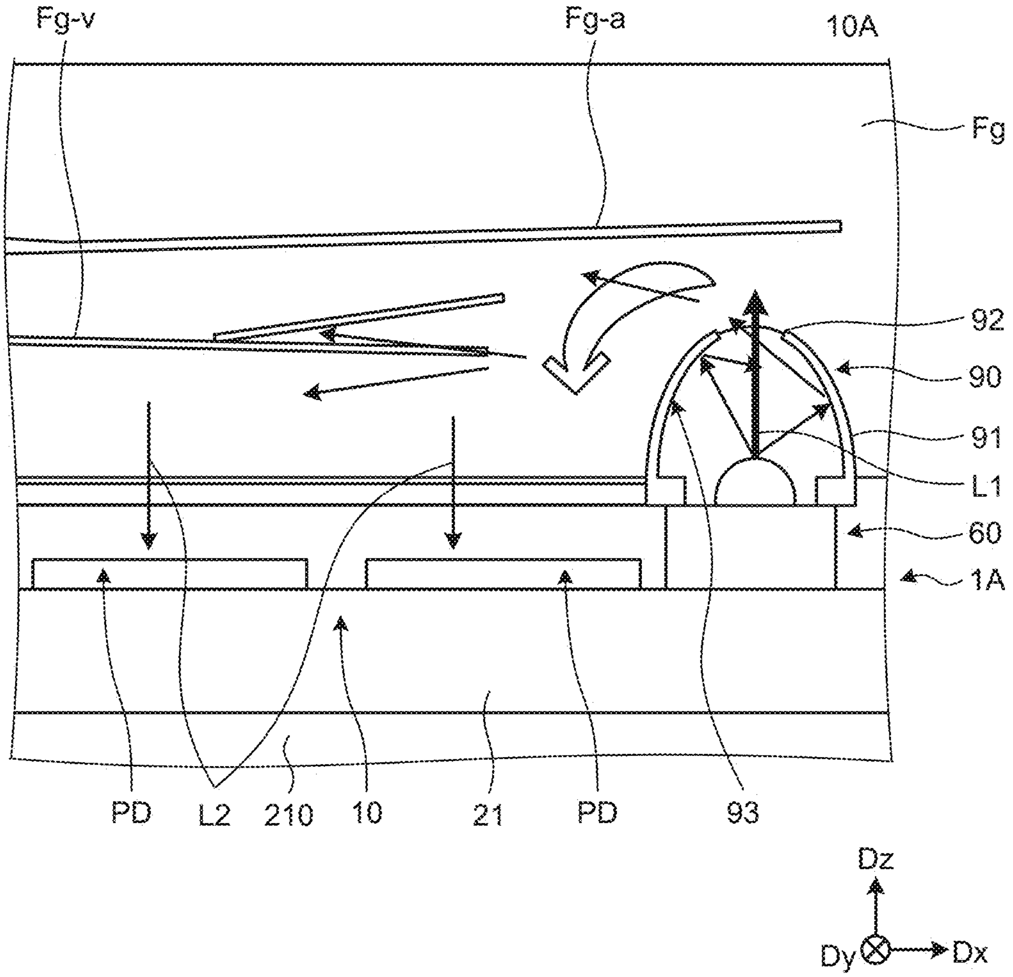
FIG. 10 is a schematic sectional view illustrating an exemplary configuration of the detection device taken along section E-E illustrated in FIG. 8.

The following describes an exemplary effect of light of the detection device 1A of the second embodiment. FIG. 10 is a schematic sectional view illustrating an exemplary configuration of the detection device 1A taken along section E-E illustrated in FIG. 8. In the detection device 1A illustrated in FIG. 10, the distance D between the light source 60 and the optical sensor 10 is 5 mm or less. In the detection device 1A, the optical sensor 10 and the cover 90 are accommodated in the first housing 210 of the housing 200 while being provided close to each other on the sensor substrate 21.

When the light source 60 emits the light L1 while the detection device 1A is worn on the finger Fg, the detection device 1A emits the light L1 including the light reflected by the reflective layer 93 inside the cover 90 toward the finger Fg from the opening 92 of the cover 90. The light L1 enters the inside of the finger Fg through the skin and is transmitted through and reflected from the muscle tissues, the arteries Fg-a, and the veins Fg-v. The reflected light L2 obtained by reflecting the light L1 in the finger Fg travels toward the inner side of the finger Fg or toward the detection device 1A. If the optical sensor 10 of the detection device 1A is placed at a destination of the light L2 emitted outward from the finger Fg, the photodiodes PD of the optical sensor 10 receive the reflected light L2. In the detection device 1A, if the light L1 emitted by the light source 60 travels toward the optical sensor 10, the light L1 is blocked by the cover 90, so that the optical sensor 10 does not detect the light L1. Furthermore, in the detection device 1A, the cover 90 is pressed against the surface of the finger Fg, and the opening 92 of the cover 90 can be made closer to the arteries Fg-a located deep inside the finger Fg. Therefore, the beam of the light L1 from the light source 60 can be focused on the arteries Fg-a. The detection device 1A can thereby detect the information on the living body in the finger Fg or the like based on the reflected light L2 received by the photodiodes PD of the optical sensor 10, and can improve the ratio of arterial information.

Figure 11:
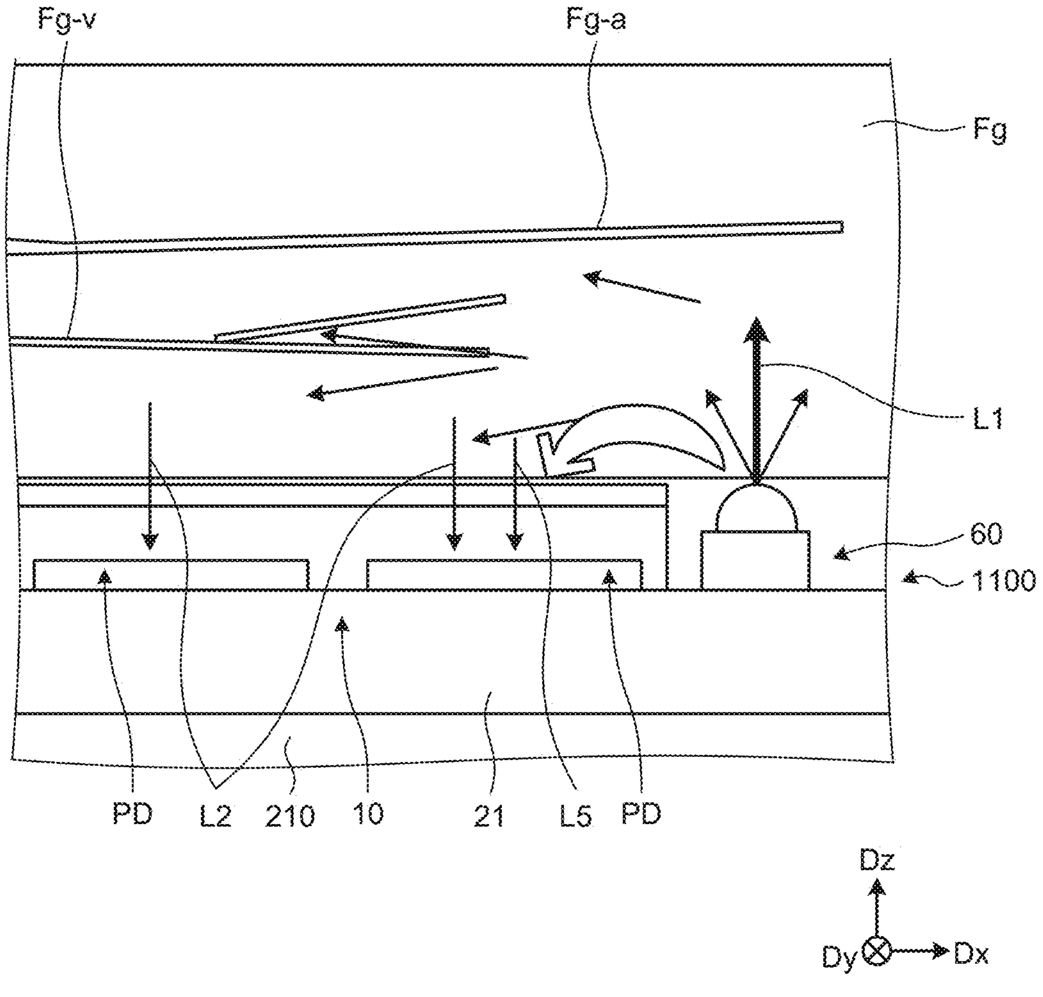
FIG. 11 is a schematic sectional view for explaining an exemplary effect of light of a comparative detection device according to the second embodiment.

In contrast, the following describes a case where the detection device 1A does not include the cover 90. FIG. 11 is a schematic sectional view for explaining an exemplary effect of light of a comparative detection device 1100 according to the second embodiment. The comparative detection device 1100 illustrated in FIG. 11 has the same basic configuration as the detection device 1A of the second embodiment, and differs from the detection device 1A in not including the cover 90.

In the comparative detection device 1100 illustrated in FIG. 11, the distance D between the light source 60 and the optical sensor 10 is 5 mm or less (for example, 4 mm). In the comparative detection device 1100, no light-blocking object is provided between the light source 60 and the optical sensor 10 on the sensor substrate 21. When the light source 60 emits the light L1 while the comparative detection device 1100 is worn on the finger Fg, the light L1 is applied to the finger Fg through the housing 200, and a part of the light L1 travels toward the adjacent optical sensor 10. For this reason, in the comparative detection device 1100, the reflected light L2 reflected by the finger Fg and received by the optical sensor 10 includes reflected light L5 not reflected by the arteries Fg-a and direct light from the light source 60.

Therefore, the accuracy of detection of the information on the living body based on the light received by the optical sensor 10 decreases.

The detection device 1A according to the second embodiment will be compared with the comparative detection device 1100. The detection device 1A can increase the reflected light L2 reflected by the arteries Fg-a of the light L1 emitted from the light source 60 into the finger Fg. In contrast, the comparative detection device 1100 is not provided with the cover 90. Thus, of the light L1 emitted from the light source 60 into the finger Fg, the reflected light L2 and the reflected light L5 are received. Therefore, the detection device 1A can increase the reflected light L2 reflected by the arteries Fg-a compared with the comparative detection device 1100. In addition, the detection device 1A can accommodate the light source 60 and the optical sensor 10 close to each other in the housing 200, thus making it possible to improve the light use efficiency. As a result, even when the distance D between the light source 60 and the optical sensor 10 is set to 5 mm or less, the detection device 1A can reduce the loss of the amount of light reaching the optical sensor 10. Therefore, the accuracy of detection of the light of the light source 60 in the ring-shaped housing 200 can be improved.

In the detection device 1A, the reflectance of the reflective layer 93 of the cover 90 is set to 50% or more. This setting allows the detection device 1A to direct more light emitted by the light source 60 toward the opening 92 and increase the amount of outgoing light from the opening 92 of the cover 90 pressed against the finger Fg (living body). Therefore, the accuracy of detection of the information on the living body can be improved.

In the detection device 1A, the optical sensor 10 is organic photodiodes. This configuration allows the detection device 1 to accurately detect the light reflected by the finger Fg, using the optical sensor 10.

In the detection device 1A, the optical sensor 10 and the light source 60 are provided on the flexible printed circuit board 70; the lower electrodes 11 of the optical sensor 10 are electrically coupled to the wiring lines 26; and the wiring lines 26 are electrically coupled to the flexible printed circuit board 70. This configuration allows the detection device 1A to be manufactured by accommodating the flexible printed circuit board 70 in the housing 200, so that the productivity can be improved.

In the detection device 1A, the housing 200 is formed in a ring shape. As a result, even though the light source 60 and the optical sensor 10 are provided close to each other in the ring-shaped housing 200, the cover 90 is provided between the light source 60 and the optical sensor 10. Therefore, the detection device 1A can improve the accuracy of detection of the light emitted toward the finger Fg by the light source 60.

In the present embodiment described above, the case where each of the detection devices 1 and 1A uses the ring-shaped housing 200 has been described, but the detection devices 1 and 1A are not limited to this case. For example, each of the detection devices 1 and 1A may have a housing having a card shape, a band shape, or the like. In that case, in each of the detection devices 1 and 1A, a side of the housing that makes contact with the human body is the irradiation side of the light source. In each of the detection devices 1 and 1A, the optical sensor may use silicon photodiodes.

In the present embodiments described above, the cases where the detection device 1 includes the reflective member 80 and the detection device 1A includes the cover 90 have been described, but the present disclosure is not limited to these cases. For example, when a plurality of the optical sensors 10 are provided adjacent to the light source 60 in the circumferential direction 200C of the housing 200, one detection device may have a configuration including the reflective member 80 and the cover 90 depending on the distance D between the light source 60 and the optical sensor 10.

The components in the embodiments described above can be combined as appropriate. Other operational advantages accruing from the aspects described in the present embodiments that are obvious from the description herein, or that are conceivable as appropriate by those skilled in the art will naturally be understood as accruing from the present invention.

What is claimed is:

1. A detection device comprising:
- a housing;
- a light source that is provided in the housing so as to be capable of irradiating an irradiation side outside the housing;
- an optical sensor that is provided so as to be arranged alongside the light source in a first direction of the housing and is capable of detecting light incident from the irradiation side of the light source; and
- a reflective member that is provided in the housing so as to be located between the light source and the optical sensor and is capable of reflecting the incident light toward the irradiation side of the light source, wherein
- in the first direction that is parallel to a circumferential direction of the housing, the light source is disposed adjacent to the reflective member disposed adjacent to the optical sensor that has an end close to a reflective member,
- a length between the end and the light source is within a quarter of an inner circumference of the housing, in the first direction, and
- the reflective member is mounted on a flexible printed circuit board in the housing.

2. The detection device according to claim 1, wherein a distance between the light source and the optical sensor is 5 mm or more.

3. The detection device according to claim 2, wherein the reflective member has reflectance of 50% or more.

4. The detection device according to claim 3, wherein the light source is configured to emit any one of near-infrared light, red light, and green light.

5. The detection device according to claim 4, wherein the optical sensor is an organic photodiode comprising a sensor substrate, a lower electrode, a lower buffer layer, an active layer, an upper buffer layer, and an upper electrode.

6. The detection device according to claim 5, wherein
- the light source and the optical sensor are provided on the flexible printed circuit board,
- the optical sensor has a configuration in which wiring, an insulating layer, the lower electrode, the lower buffer layer, the active layer, the upper buffer layer, and the upper electrode are stacked on the sensor substrate in the order as listed, and
- the lower electrode is electrically coupled to the wiring, and the wiring is electrically coupled to the flexible printed circuit board.

7. The detection device according to claim 6, wherein the housing is formed in a ring shape.

* * * * *